(12) United States Patent
Kronmueller et al.

(10) Patent No.: US 9,821,395 B2
(45) Date of Patent: Nov. 21, 2017

(54) METHOD FOR PRODUCING A PIN FOR A FEEDTHROUGH OF AN ELECTROMEDICAL IMPLANT AND A FEEDTHROUGH

(71) Applicant: BIOTRONIK SE & Co. KG, Berlin (DE)

(72) Inventors: Daniel Kronmueller, Nuremberg (DE); Michael Arnold, Erlangen (DE); Josef Teske, Hallstadt (DE); Peter Meidlein, Nuremberg (DE)

(73) Assignee: BIOTRONIK SE & Co. KG, Berlin (DE)

( * ) Notice: Subject to any disclaimer, the term of this patent is extended or adjusted under 35 U.S.C. 154(b) by 11 days.

(21) Appl. No.: 14/741,597

(22) Filed: Jun. 17, 2015

(65) Prior Publication Data
US 2016/0001387 A1 Jan. 7, 2016

Related U.S. Application Data

(60) Provisional application No. 62/021,212, filed on Jul. 7, 2014.

(51) Int. Cl.
*B23K 37/00* (2006.01)
*B23K 1/00* (2006.01)
(Continued)

(52) U.S. Cl.
CPC .......... *B23K 1/0008* (2013.01); *A61N 1/3754* (2013.01); *B23K 31/02* (2013.01); *C25D 7/0614* (2013.01)

(58) Field of Classification Search
CPC ...... A61N 1/3754; H01R 43/16; H01R 43/20; H01R 43/24; H01R 43/28
See application file for complete search history.

(56) References Cited

U.S. PATENT DOCUMENTS 3,545,606 A    12/1970   Bennett et al.
4,627,682 A * 12/1986   Hehl ...................... H01R 43/16
                                                       29/879
(Continued)

FOREIGN PATENT DOCUMENTS

EP    2 371 418      10/2011
EP    2 529 790      12/2012
GB      863386   *   3/1961

OTHER PUBLICATIONS

European Search Report and Annex to the European Search Report on European Patent Application No. EP 15 17 3082, dated Nov. 5, 2015 (7 pages).

*Primary Examiner* — Carl Arbes
(74) *Attorney, Agent, or Firm* — Buchanan Ingersoll & Rooney PC

(57) ABSTRACT

A method for producing a pin for a feedthrough for an electromedical implant. A pin is produced using the following method steps: creating a foil-, sheet- or strip-shaped semi-finished product by joining at least one first layer element including an electrically conducting, preferably biocompatible, material in foil, sheet or strip form and at least one second layer element including a solder and/or an easily soft-solderable material, preferably in wire, sheet or strip form, or by applying the at least one second layer element onto the at least one first layer element; and at least partially detaching a pin, or a set of multiple pins connected to a connecting web 46, from the semi-finished product. A method is also provided for producing a feedthrough and an electromedical implant and to a pin, a feedthrough or an implant produced in the corresponding manner.

24 Claims, 17 Drawing Sheets

(51) Int. Cl.
  *B23K 31/02*  (2006.01)
  *C25D 7/06*  (2006.01)
  *A61N 1/375*  (2006.01)

(56) References Cited

U.S. PATENT DOCUMENTS

| | | | | |
|---|---|---|---|---|
| 4,684,203 | A | * | 8/1987 | Bihler .................. H01R 12/585 29/876 |
| 4,729,504 | A | | 3/1988 | Edamura |
| 4,825,541 | A | * | 5/1989 | Czeschka ................ H01R 43/16 29/874 |
| 5,230,713 | A | * | 7/1993 | Schauer ................ B60R 16/027 29/856 |
| 2001/0013172 | A1 | * | 8/2001 | Wilczek .............. H01L 21/4875 29/884 |
| 2005/0060003 | A1 | * | 3/2005 | Taylor .................. A61N 1/3754 607/36 |
| 2008/0257581 | A1 | | 10/2008 | Masago et al. |
| 2012/0200011 | A1 | | 8/2012 | Pavlovic |

* cited by examiner

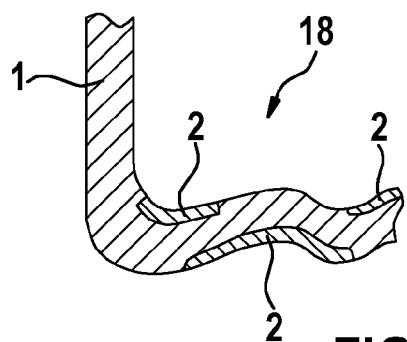
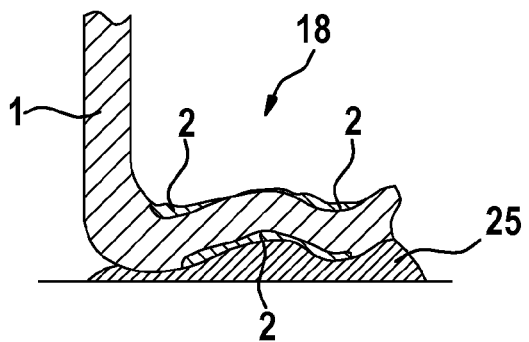
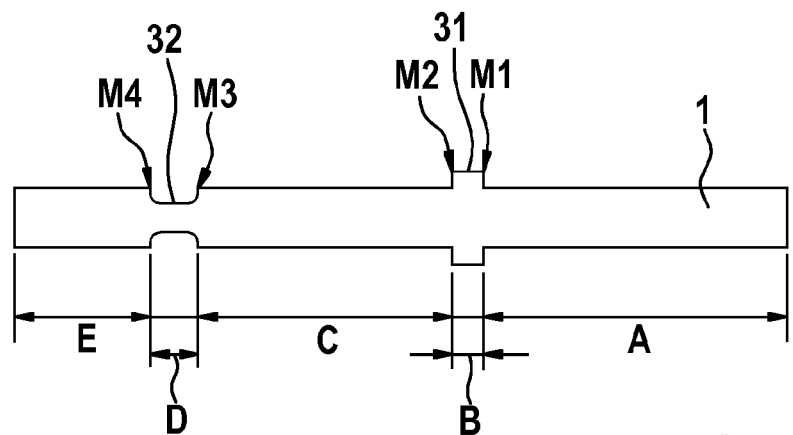

METHOD FOR PRODUCING A PIN FOR A FEEDTHROUGH OF AN ELECTROMEDICAL IMPLANT AND A FEEDTHROUGH

CROSS-REFERENCE TO RELATED APPLICATIONS

This patent application claims the benefit of U.S. Provisional Patent Application No. 62/021,212, filed on Jul. 7, 2014, which is hereby incorporated by reference in its entirety.

TECHNICAL FIELD

The present invention relates to a method for producing a pin for an electromedical implant, to a method for producing a feedthrough and an electromedical implant, and to a pin produced in the corresponding manner, to a feedthrough produced in the corresponding manner, and to an implant.

BACKGROUND

Medical or active implants are known from the state of the art in great diversity. In the context of the present invention, an electromedical implant shall be understood to mean an implant that comprises a power supply unit (such as, for example, a battery) and electrical and/or electronic components such as, for example, a printed circuit board, which are disposed in a housing that is hermetically sealed. Such electromedical implants are, for example, cardiac pacemakers, defibrillators, neurostimulators, leadless pacemakers, cardioverters, drug pump implants, cochlear implants or other hermetically encapsulated electronic products for implantation in a human or an animal body.

Such implants are frequently connected to electrode lead wires, which after implantation in a human or an animal body treat the same, for example, by transmitting and/or delivering stimulation pulses and/or defibrillator shocks to certain sites of the body, or which are used to detect electrical potential of and from sites of the body. For this purpose, an electrical connection must be established between the electrical and/or electronic components disposed in the housing interior and the respective electrode lead wire. This electrical connection is generally implemented by way of a feedthrough and/or what is known as a header. Such a feedthrough ensures at least one electrical connection between the interior of the housing and the exterior, while also hermetically sealing the housing of the implant. The header, attached via the feedthrough, continues the electrical connection of the feedthrough to a contact point and is used to plug the at least one electrode lead wire into a corresponding, and usually standardized, socket. An electrical contact is thus established between the implant and the connecting piece of the electrode lead wire at the contact points of the bushing. A feedthrough and a header can also be implemented in a single component. In this case as well, such a combined component is generally referred to hereafter as a feedthrough.

Such feedthroughs generally comprise an electrically insulating body, this being the insulator, which is frequently produced from ceramic or other similar material and implements the hermetic sealing of the housing. The insulator often has a flange for this purpose, by way of which the insulator is inserted into the open end of the housing of the implant. The insulator furthermore frequently includes continuous cut-outs, such as, for example, boreholes, in each of which a connection pin (hereinafter abbreviated as pin) is provided, which is also referred to as a terminal pin. The pin is frequently attached in the cut-out, which can additionally comprise a feedthrough sleeve, by way of high-temperature brazing. The pin is used to establish an electrical connection between the housing interior and the header or the electrode lead wire. Such a feedthrough comprising a pin is known from the published prior art European Patent Application No. EP 2 371 418, for example, which shows and describes in particular a feedthrough comprising a terminal pin. The pin comprises a first section made of a biocompatible material and a second section made of a material that can be joined using low energy. The second section is to be disposed in the interior of the housing of the implant.

Brazing is a known thermal process for integrally joining materials, the process being usable to establish an electrical connection and being carried out using a solder. Depending on the temperature, a person skilled in the art distinguishes between three known methods. The process is referred to as soft soldering in the temperature range up to 450° C. Known soft solders are Sn63Pb37, Sn96Ag4 and Au80Sn20, for example. The process is referred to as brazing in the temperature range between 450° C. and 900° C. For this, silver or brass solders are frequently used (such as, for example, L-Ag44 (Ag44Cu30Zn26)). The process is referred to as high-temperature brazing at temperatures above 900° C. In medical technology, high-temperature solders include Au (99.95), AuAg8, AuPt10 and Ti60Ni25Cu15, for example.

Conventionally, the pin disposed in the feedthrough is directly connected to a terminal of a printed circuit board by way of soft soldering or welding so as to establish the electrical connection with the electronic circuit located on the printed circuit board. The published prior art European Application No. EP 2 529 790 discloses the use of a connector, which is attached to the terminal pin by way of a clip connection. The connector moreover comprises a sleeve, which surrounds the terminal pin and is fixed on a printed circuit board disposed in the interior of the implant by way of soft soldering or welding so as to establish an electrical connection.

In the production of such feedthroughs and implants, in particular, inserting and brazing the pin and establishing the electrical connection between the pin and the printed circuit board are complex and cost-intensive. The elements of a pin are initially produced individually and then assembled and joined manually.

For example, gold solder rings or sleeves are produced separately prior to brazing the pin to the feedthrough and are manually assembled individually with a pin. The problem that exists with this process is that the entire feedthrough must be removed if a solder ring or a solder sleeve falls off during mounting. In the case of multi-pole feedthroughs, the costs resulting from mounting errors are therefore very high. Additionally, the problem exists that the product groups encompassing the pin and solder arrive individually in the receiving department of the producing company. Until processing, these product groups must be stored separately from other components. This likewise creates high complexity for each component in materials management. Moreover, each component must be independently tested for defects. The complexities for individual processes that are related to this (stamping, cleaning, sorting, packaging, etc.) exceed the material value of the respective component several fold.

Using an upstream high-temperature brazing process, the solder can be brazed onto the wire pin. However, this is a multi-stage joining process using the individual components, in which overall no savings are achieved in terms of labor time or cost.

Additionally, the option exists to coat the pins with solder material by way of electroplating or by way of coating methods. However, the galvanic coating of wire sections in the form of bulk material is likewise very complex, since a uniform layer thickness can only be assured by previously separating and aligning the pins. Moreover, inclusions from the electroplating solution may occur. Such an electroplating solution additionally often represents a dangerous or toxic substance, which is undesirable in the field of medical technology and may be problematic in terms of disposal.

If PVD or CVD methods are used for coating, the maximally achievable layer thickness is limited to several 10 μm due to economic efficiency. This method likewise necessitates separation of the pins. It may be necessary to mask the pins for the application process, making the method not cost-efficient for the application of a sufficient amount of solder.

The production process is also initially separate on the implant interior at the contact point between the pin and the printed circuit board, which is normally joined by way of a soft solder joint using, for example, SMT methods. The required soft solderability for the SMT process is created by adding further components during or after the high-temperature brazing process.

Overall, bulk material is problematic to process in production since the respective components must be singulated, aligned and optionally oriented prior to processing, which represents an additional process step that is required for measuring or testing tasks in a partially or fully automated production plant.

The present invention is directed toward overcoming one or more of the above-mentioned problems.

SUMMARY

Therefore, it is an object of the present invention to simplify the production of the feedthrough and of an electromedical implant and to design the process to be more cost-effective.

At least the above object is achieved by a method for producing a pin for the feedthrough of an electromedical implant, comprising the following steps:
  creating a foil-, sheet- or strip-shaped semi-finished product by joining at least one first layer element comprising an electrically conducting, preferably biocompatible, material in foil, sheet or strip form, and at least one second layer element comprising a solder and/or a easily soft-solderable material, preferably in wire, sheet or strip form, or by applying the at least one second layer element onto the at least one first layer element; and
  at least partially detaching a pin, or a set of multiple pins connected to a connecting web, from the semi-finished product.

The method according to the present invention is based on the realization by the inventors that the production process of the pin must be designed fundamentally differently so to achieve simplifications and/or cost savings in the production of the feedthrough and of the implant. The production process has now been modified in such a way that initially the elements of the pin in foil, sheet or strip form are joined. The pins are singulated subsequently by detachment from the foil, the sheet or the strip.

The advantage of the method according to the present invention is, in particular, that bulk material processes, or individual manual assembly processes of small parts, are avoided when the pins or pin sets are separated later in the process chain, such as not until after high-temperature brazing. The method according to the present invention can additionally be used to adjust the content of the electrically conducting material and of the high-temperature solder or soft-solderable material within narrow limits in a targeted manner. While the method according to the present invention increases the use of material due to the joining process at the raw material level, it is possible to considerably increase the quality due to the comparatively simple and reliable joining process and easier introduction of the pin into the feedthrough and simpler brazing, and it is thus possible to effectively contribute to lowering the reject rates. In the case of feedthroughs that can be brazed using SMT (surface mounting technology) and using ten signal pins, for example, the mounting time decreases by approximately thirty percent per feedthrough.

Many error patterns that arise from a manual mounting process of the individual components in relation to each other can be avoided (such as, for example, "coaxiality", "contact element missing", etc.). As a result, testing for such error patterns in production becomes considerably easier.

Due to a collective separation process from previously joined materials, it becomes easier to coordinate component tolerances of the feedthrough components with each other during the design phase, since some parts are already being produced at identical tolerances.

Moreover, visual inspection and dimensional testing likewise become easier since they can be carried out at least partially already on the semi-finished product. In this way, previously still very complex testing tasks that took place only sporadically can be broken down into several independent individual inspections. By joining the functional elements of the pin in a separate process, the occurrence of errors in the joining process of the pin in the feedthrough is minimized. By sorting faulty pins already after the pins have been produced, it is possible to prevent these from being processed into feedthroughs. This increases the economic efficiency of the joining processes.

Overall, the procedure according to the present invention, in which the different pin materials are already joined together in the semi-finished product stage, combines multiple cost-intensive individual manual processes into few, well-controllable process steps, which can be easily automated. By redesigning the processes, the pin can be produced cost-effectively both in the form of strip material in average quantities and using reel-to-reel methods in large quantities.

In a preferred exemplary embodiment, only a portion of the contour of the pins is initially detached from the semi-finished product (for example, cut out by way of punching) prior to fully detaching the pin, or a set of multiple pins, from the semi-finished product and subsequently at least a sub-region of the pin is formed (such as, for example, by embossing, bending, etc.). In this way, the forming process can be achieved particularly easily since the pin is still attached to the semi-finished product. Details with regard to the forming processes are described hereafter. The pin is fully detached from the semi-finished product after the forming process, such as, for example, by way of punching or along a predetermined breaking point.

The first layer element and the second layer element are connected to each other in a form-locked or integral manner preferably during production of the foil-, sheet- or strip-shaped semi-finished product. Joining may be carried out with the application of heat, wherein inter-diffusion of the materials of the two layer elements can be influenced by the materials that are used, the layer geometry and the process parameters that are used (such as, for example, diffusion heating).

As an alternative, the at least one second layer element can be applied and integrally joined to the first layer element using a vacuum technology coating method (PVD or CVD) or a galvanic coating can be applied to the first layer element. Vacuum technology coating methods generate coating thicknesses between 0.1 µm and 10 µm; typical layer thicknesses in the range of 0.1 µm to 10 µm are likewise achievable by way of electroplating:

The at least one first layer element is preferably made of a biocompatible electrically conducting material in foil, sheet or strip form, for example, comprising an element from the group consisting of Nb, Pt, Pd, Ta, Zr, Ir, Ru and Hf, or an alloy thereof, preferably the at least one first layer element comprises PtIr10, PtRu10 and/or surgical stainless steel (such as, for example, 316L). Moreover, the at least one first layer element can comprise at least one element from the group consisting of Mo, Wo, Cr, V and Al, or an alloy thereof, such as FeNi, FeNiCo, FeCr.

The at least one first layer element is preferably cleaned and degreased prior to being joined with the at least one second layer element. It is also preferred if the first layer element is a foil or a sheet comprising at least one step and/or groove and/or comprising multiple material layers (multi-layer sheet).

After the semi-finished product has been produced, it can be measured, post-processed and optionally sorted. Moreover, intermediate steps such as cleaning, pickling, polishing or the like can be carried out at any time.

For example, the at least one second layer element comprises a high-temperature solder, such as at least one element from the group Au and Ag, or an alloy thereof (such as AuNi, AuPt10, AgCu, AuCu) and/or an active solder (such as AuCuNi, Ti70Ni15Cu15, Ag68Cu26Ti6, Ti67Ni33) and/or a glass solder, which is preferably designed to be biocompatible. Suitable glass solders are glasses having a reduced softening point and a defined composition.

The second element can comprise Cu, Ag, Au, Ni, Pd, Pt, Ir, Fe or alloys, in particular, CuAg0.10, CuAg.10P, CuTeP, for example, as soft-solderable materials. As an alternative, the second layer element can be used as a layer system made of these materials.

In a preferred exemplary embodiment, essentially known methods such as, for example, cladding, rolling, brazing or roller seam welding can be used to join the at least one first layer element to the at least one second layer element.

The detachment according to the present invention of a pin, or of a set of multiple pins connected to a connecting web, from the semi-finished product or the blank is preferably carried out by way of fine blanking, punching, chemical milling, laser cutting or water jet cutting. The respective method that is used depends on the geometry and the tolerance requirements for the particular pin, or set of multiple pins.

It is advantageous to form layers as solder inhibitor layers or secondary layers on sub-regions or regions of the semi-finished product.

For example, a thin layer (layer thickness at least 10 µm, and preferably at least 50 µm), including at least one element from the group consisting of Al, Mg, Ca, Zr and Y, or an alloy of these elements, is applied to the at least one first layer element, the thin layer preferably being applied to at least a portion of the surface of the at least one first layer element, in addition to the at least one second layer element comprising the solder, and optionally being joined thereto. For this purpose, the above-mentioned joining methods can be used. The described layers can preferably be oxidized both selectively and in a planar manner. Areas that are not to be coated are masked using photoresist or paint. Masked regions remain protected from oxidation and can thus be better wetted with solder than the oxides. Oxidation during a wet-chemical treatment (such as cleaning of the pins) to obtain a metal oxide layer, such as an aluminum oxide layer, an yttrium oxide layer or a zirconium oxide layer, which assumes the function of a solder inhibitor layer or solder barrier, is particularly advantageous. After oxidation, the photoresist can be removed from the component and the normal chemical treatment can be carried out.

It is further advantageous if the semi-finished product additionally comprises at least one third layer element including an insulator or a ductile metal, which is joined with the at least one first layer element and/or the at least one second layer element. The at least one first layer element including a metallic conductor and the at least one third layer element including an insulator preferably form a base material, which is designed as a multi-layer sheet. A pin comprising such a base material can be used as a multi-pole feedthrough pin. The at least one first layer element and/or the at least one second layer element having a wire, sheet or strip form are joined with the at least one third layer element in wire, sheet or strip form by way of the above-described joining methods. The ductile material ensures better formability during forming (such as, for example, circular embossing) and prevents the solder of the second layer element from laterally flowing away.

It is advantageous if the surfaces are planar, in particular in the case of punching or embossing. For this purpose, a sacrificial layer made of a ductile material (such as aluminum) can be applied to the at least one first layer element, the sacrificial layer being used to fill cavities and equalize the height between the uppermost first layer element and the uppermost second layer element. After forming, the sacrificial layer can be removed very easily from the other layer elements in a cleaning process using a lye. Preferably sodium hydroxide having a concentration of 10 to 45% at a temperature of 30 to 70° C. is used.

In a further preferred exemplary embodiment, a top coat is applied to the semi-finished product for improved soft solderability or as a protective layer, preferably by way of an electroplating bath, prior to and/or after the optionally at least partial detachment of the pin, or of the set of multiple pins, from the semi-finished product.

The top coat for improved soft solderability is preferably provided at least partially in the region in which the at least one second layer element comprising a soft-solderable material is disposed. In this way, it can be ensured, for example, when using nickel as the soft-solderable material, that no exposed nickel surfaces exist on the pin, from which nickel can be carried over in an uncontrolled manner during further processing steps, and that the soft-solderable material is encapsulated by a noble metal (such as Au). Moreover, the layer thickness can be homogenized by another coating with the second layer element or an alloying constituent after the process step. It can thus be ensured that the pin can be evenly wetted from all sides, which is to say also at the edges detached from the semi-finished product, with the soft solder when the pin is brazed to the printed circuit board or into the cut-out of the feedthrough. Such a top coat can be made of Au or Pd or an alloy made of other noble metals, for example. Depending on the material to be joined and the production process, different surface finishing methods (such as, for example, ENIG—electroless nickel immersion gold, ENEPIG—electroless nickel electroless palladium immersion gold, or HAL gold—hot air leveled gold) are possible.

A protective layer can be applied to the surface of the first and/or second layer elements as a seal until further processing, wherein a polymer or an organic protective film (OSP—organic surface protection) is used for this purpose. Known protective films can be completely or selectively deposited onto the pin after partial or complete detachment. Typical layer thicknesses are 0.2 µm to 0.6 µm and include substituted imidiazoles and/or triazoles, for example. The protective film typically prevents the base material from oxidizing for several months during storage and pyrolyzes immediately prior to or during the brazing or soft soldering process. The protective film is applied to the pin sections by way of coating (such as, for example, painting, dipping, etc.) or using the reel-to-reel method immediately after cleaning or pickling.

It has been found to be particularly advantageous in one exemplary embodiment of the method according to the present invention to form the pin prior to or after being at least partially detached from the semi-finished product, and preferably in such a way that the at least one second layer element at least partially surrounds the pin. This is advantageous since a sharp separating edge is created when detaching the pin, or of the set of multiple pins, from the semi-finished product, and for example, the deposited solder is not, or only partially, disposed on the cutting surface. The solder distributes around the pin when the pin is brazed to the feedthrough. So as to achieve a more homogeneous distribution of the solder around the pin, it is therefore advantageous to distribute or spread the deposited solder over all sides of the pin by way of forming. The spreading ensures that the solder cone around the pin closes during melting, thereby creating a reliable connection. The likelihood of flaws in the solder is thus minimized. The same applies analogously to the at least one second layer element comprising a soft-solderable material.

It is further advantageous that the pin, or each pin of the set of multiple pins, is formed after the at least partial detachment in such a way that at least one, preferably circumferential, protrusion and/or at least one recess are created, wherein the protrusion and/or the recess are located in each case on the side surface (lateral face) of the particular pin. Such a protrusion or stop allows the pin to keep its position in the feedthrough during the brazing process, or it allows correct positioning of the pin in the feedthrough to be achieved. A recess can additionally serve as a solder stop.

It is further advantageous if the at least partial detachment takes place in a direction that is substantially perpendicular (transverse) to the direction of joining of the at least one first layer element with the at least one second element and/or the at least one third layer element. In this way, for example, the rolling direction, the cladding direction, which is to say the joining direction of the materials, is substantially perpendicular to the longitudinal and punching directions of the pin, whereby structural flaws or leakage paths are avoided.

It is further advantageous if a section of the pin is shaped to be round after the at least partial detachment, in particular, the region of the shaft extending along the longitudinal direction of the pin which is installed in the feedthrough and by way of which the pin is inserted into the feedthrough. This is advantageous since the continuous cut-outs in the feedthrough ceramics are frequently designed to be round or circular. This results in more even brazing solder distribution during the liquid phase of the solder in the gap and in a reduction of brazing solder that is required. Circular embossing can be implemented by way of a composite progressive cutting tool, for example. In the flow region of the solder, the embossing tool is advantageously structured predominantly perpendicularly to the pin axis so that defined micro-roughness of at least 2 µm is created. Due to the shaping of the surface structure of the embossing dies, solder inhibitor layers from the uppermost layer elements can be embossed into the pin, which differ in terms of the micro-roughness and surface structure thereof from the layers located beneath.

In a further preferred exemplary embodiment, the pin is formed on at least one end section into a gull wing, J-lead or SOP-like shape after the at least partial detachment. Other shapes from microelectronics are likewise conceivable. In this way, the contact surface with the printed circuit board or the adhering amount of soft solder can be increased and the necessary withdrawal force between the printed circuit board and the feedthrough can be increased.

Efficiency during production of a feedthrough can be further increased by initially detaching only a set of multiple pins that are connected to a connecting web from the semi-finished product, wherein preferably the pins of the set are partially detached from each other. The pins of this set can subsequently be coated and/or formed together, as described above, and be attached together in the feedthrough by way of high-temperature brazing, wherein each pin is disposed in a separate cut-out. The connecting web protects the pins during transport from deformation and ensures uniform evenness during assembly across all the pins of the connecting web. After joining in the assembly, the pins are preferably separated from each other by removing the connecting web. For this purpose, a predetermined breaking point can be introduced in one end section of a pin, preferably next to the connecting web, in a preferred exemplary embodiment of the method according to the present invention. This can be implemented by introducing a notch or a continuous cut-out in this region. As an alternative, the jointly assembled pins can be shortened to the same height by an individual cutting process. For this purpose, the feedthrough is clamped on the flange and on the connecting web and is subsequently detached simultaneously across all pins.

At least the above object is further achieved by a method for producing a feedthrough for an electromedical implant, wherein a body of a feedthrough having at least one continuous cut-out is provided, moreover the above-described steps for producing a pin are carried out, and the additional step is carried out, according to which the pin, or each pin of the set of multiple pins, is connected to the inner surface of a continuous cut-out of the body by way of brazing. This method according to the present invention has the above-described advantages over the conventional methods. It is particularly preferred to subsequently separate the multiple pins of the set from each other, preferably by removing a connecting web and/or along a predetermined breaking point that was previously introduced into the pin or a common alignment.

At least the above object is further achieved by a method for producing an electromedical implant comprising a printed circuit board and using the above-described steps for producing a feedthrough, wherein subsequently each pin of the feedthrough is connected to a terminal of the printed circuit board, preferably by way of brazing or welding. Thereafter, the printed circuit board is disposed in a housing of the implant, and the feedthrough is connected to the housing in a hermetically sealed manner.

At least the above object is also achieved by a pin for an electromedical implant that is produced or producible using an above-described method.

At least the above object is moreover achieved by a feedthrough for an electromedical implant that is produced or producible using an above-described method.

At least the above object is moreover achieved by an electromedical implant that is produced or producible using an above-mentioned method.

The method according to the present invention for producing a pin and a feedthrough and an electromedical implant, and pins and feedthroughs thus produced, are described hereafter based on Figures. All features illustrated and/or described form the subject matter of the present invention, regardless of how they are combined in the claims or of their dependency reference.

Further features, aspects, objects, advantages, and possible applications of the present invention will become apparent from a study of the exemplary embodiments and examples described below, in combination with the Figures, and the appended claims.

DESCRIPTION OF THE DRAWINGS

In the schematic Figures:

FIGS. 21-24 show views from the side of end sections of further exemplary embodiments of a pin according to the present invention prior to being brazed to the terminal of a printed circuit board (FIG. 19 and FIG. 21) and after brazing (FIG. 22 and FIG. 24);

FIGS. 25-47 show views from the side of further exemplary embodiments of pins according to the present invention;

DETAILED DESCRIPTION

Referring to the Figures, in one exemplary embodiment of the method according to the present invention, a first layer element 1 in the form of a sheet or strip made of a biocompatible electrically conducting material (such as, for example, niobium) is initially cleaned with a solvent (such as, for example, acetone) and degreased. A second layer element 2 made of a solder (such as, for example, Au solder) or a soft-solderable material (such as, for example, nickel) is applied to at least one side of the first layer element 1. The second layer element (solder layer) 2 is connected to the first layer element 1, in particular, in a form-locked or integral manner; for this purpose, it is advantageous if the first layer element 1 includes a stop or a groove into which the second layer element 2 can be fitted in a form-locked manner and positioned in a relative manner on the first layer element 1. The width of the groove must be at least as large as the second layer element 2 and the linear expansion caused by thermal expansion. The second layer element 2 is joined onto the first layer element 1. This is done by way of brazing, for example. To this end, it is advantageous to employ a multi-stage brazing process in which first the second layer element 2 having a higher melting point is joined onto the first layer element 1. For example, first the nickel layer element is joined at a temperature of 1100 to 1380° C. Thereafter, the second layer element 2 made of gold solder is brazed on at a temperature of 950 to 1090° C.

Figure 1:
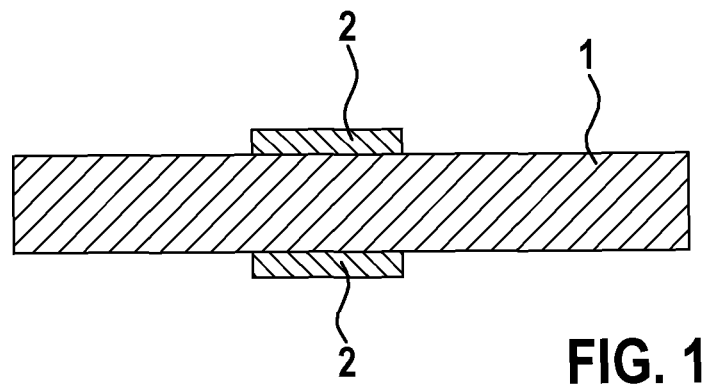
FIG. 1 shows a cross-section through a semi-finished product in the form of a strip for a pin according to the present invention of a first exemplary embodiment.

As an alternative, it is possible to employ other joining methods, such as, for example, cladding, hot pressure welding, cold roll bonding or roller seam welding. After every joining step, the joining region is inspected. For this purpose, for example, integrated visual inspection, X-ray inspection or thermography is suited, so as to detect faulty strip regions and eliminate these from further processing using an automated process. The width of the strip for the first layer element 1 is preferably at least the length of the pin to be cut out, plus lateral surfaces that are used to guide the strip. The guide surfaces of the strip for the first layer element 1 are preferably provided with openings so as to allow very precise positioning of the strip in the range of several hundredths of a millimeter or less. So as to enable mechanical guidance, it is helpful to provide boreholes, or clearances or recesses, in the sides of the strip or sheet, which can be used as centering elements or stops. The strip for the first layer element 1 is preferably even wider and, more particularly, so wide that a number of pins can be cut out of the strip. The thickness of the strip for the first layer element 1 preferably corresponds to the thickness of the first layer element 1 from which the pin will later be made, or is slightly thicker or thinner, so as to compensate for changes in thickness due to rolling, cladding or hot pressure welding, soldering or roller seam welding and the like. Comparable considerations apply to the second layer element 2 and further layer elements, wherein the strips of the further layer elements are fed without additional lateral surfaces in the form of a sheet or wire and are applied to the first layer element 1. A semi-finished product thus produced is shown in FIG. 1, and in section A of FIG. 60, wherein in the exemplary embodiment shown in FIG. 1 the top and bottom sides of the first layer element 1 are provided in each case with a second layer element 2. The solder layer is thus applied to both sides of the first layer element 1. Thereafter, a pin is at least partially detached from the semi-finished product, such as by way of, for example, punching, chemical milling, laser cutting or water jet cutting. The width of a section of the semi-finished product thus detached, as it is also shown in FIGS. 2-3 or in section B of FIG. 60, for example, is approximately 0.1 to 2 mm, and the length is approximately 0.5 to 50 mm.

Figure 2:
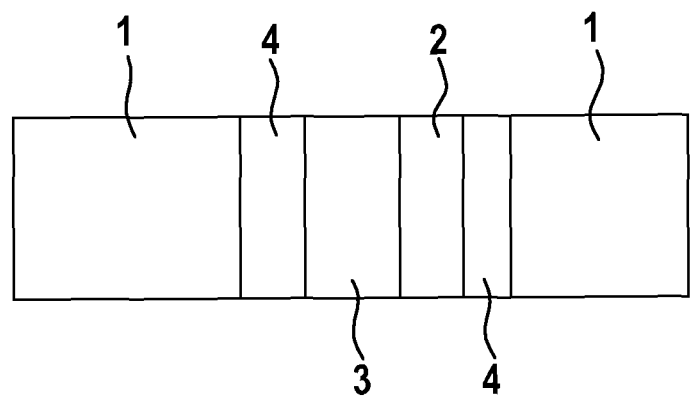
FIG. 2 shows a view from above of a pin according to the present invention of a second exemplary embodiment after it has been detached from the semi-finished product.

FIG. 2 shows a further exemplary embodiment of a pin detached from a semi-finished product, wherein additionally the flow region or melting region of the solder 3 (made of niobium, for example) is illustrated on the first layer element 1 to the right of the second layer element 2, which preferably represents a solder layer (made of gold, for example), and an anti-wetting layer element 4 (solder inhibitor layer) (zirconium oxide) is applied both to the left of the adhesion layer element 3 and to the right of the second layer element 2. The surface is adjusted in a targeted manner in the flow region of the solder 3 by way of, for example, rolling or embossing so as to improve adhesion between the solder and the third layer element. It is advantageous to adjust the roughness in the region 3 in a defined manner. It is advantageous in particular to design the micro-roughness in the solder flow region 60° to 120° perpendicularly to the pin axis.

The solder layer 2 is made of high-temperature solders such as Au, AuAg8, AuPt10 or Ti60Ni25Cu15, for example. The anti-wetting layer element 4 acts as a brazing stop and is made of ceramic layers or ceramic-containing layers, for example, such as $Al_2O_3$, $ZrO_2$, $TiO_2$, and the like, or graphite or graphite-containing layers, or metals, or the alloys thereof, which do not have a wetting effect for the brazing solder of the second layer element 2. After (high-temperature) brazing, the anti-wetting layer elements 4 can be removed, for example, by way of brushing, wet cleaning, chemical etching and the like.

Figure 3:
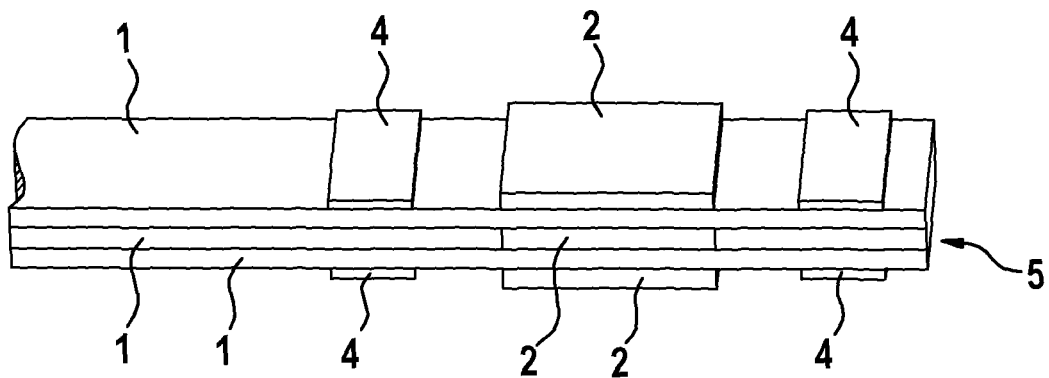
FIG. 3 shows a perspective view of a further exemplary embodiment of a pin according to the present invention after it has been detached from the semi-finished product.

An anti-wetting layer element 4 is also provided in the exemplary embodiment shown in FIG. 3, however at a distance from each side of the second layer element 2 (made of Au solder, for example). The base layer comprising the first layer element 1 is composed of three electrically conducting layers disposed on top of each other in this exemplary embodiment, wherein in the region in which a solder layer is applied to the outside of the electrical conductor, a second layer element 2 in the form of a solder layer (such as, for example, Au solder) is also provided on the inside, between two first layer elements (electrically conducting layers) 1. This has the advantage that a solder material is also disposed on the separating edge 5 that is visible from the front.

Figure 4:
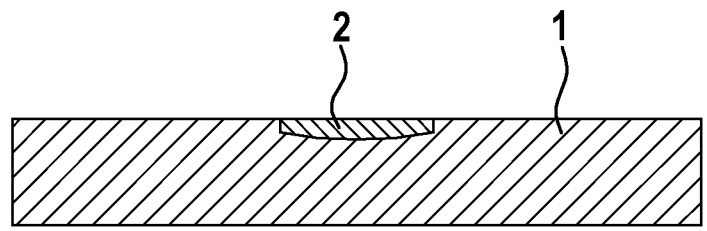
FIGS. 4-17 show further cross-sections through semi-finished products in the form of a strip for further exemplary embodiments of pins according to the present invention.
Figure 5:
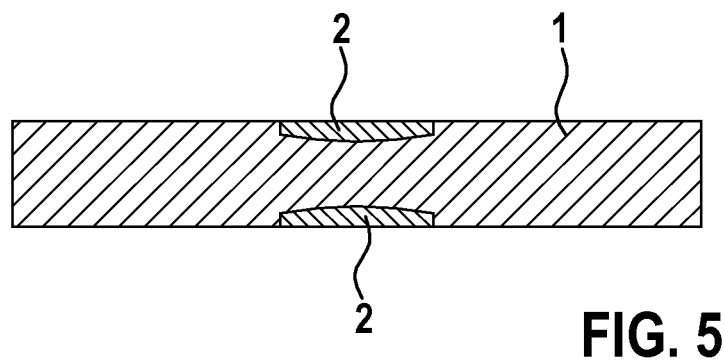

FIGS. 4-5 show semi-finished products for pins according to the present invention, which comprise the second layer elements 2 in a depression of the first layer element 1, so that the first layer element 1 extends flush with the top side of the electrically conducting layer. During production, the first layer element 1 is produced from multiple layers, or a groove of approximately 80% to 120% the depth of the second layer element 2 is provided.

The width of the groove must be at least as large as the second layer element 2 and the linear expansion caused by thermal expansion. The second layer element 2 is joined onto the first layer element 1. This is done by way of brazing, for example. The solder wets the side walls of the first layer element 1 under a meniscus. Subsequent processes such as, for example, burnishing, polishing or grinding can be used to compensate for differences in height of the solder region and uneven areas from the joining process.

Figure 6:
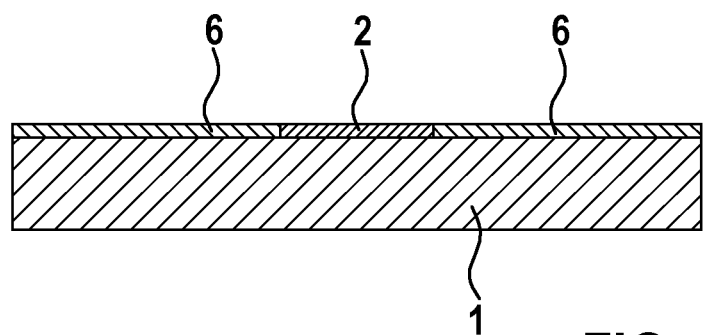

FIG. 6 shows a semi-finished product in which the material of the first layer element 1 is sealed with respect to oxidation by way of a top coat 6 in the form of a polymer layer or an OSP layer. The material of the top coat 6 is applied to the surface of the first layer element by way of painting. Immediately before processing, the top coat 6 can be partially or completely removed, for example, by way of solvents (such as acetone). As an alternative, the OSP layer pyrolizes and can be removed thereafter, such as, for example, by way of brushing, wet cleaning, chemical etching and the like.

Figure 7:
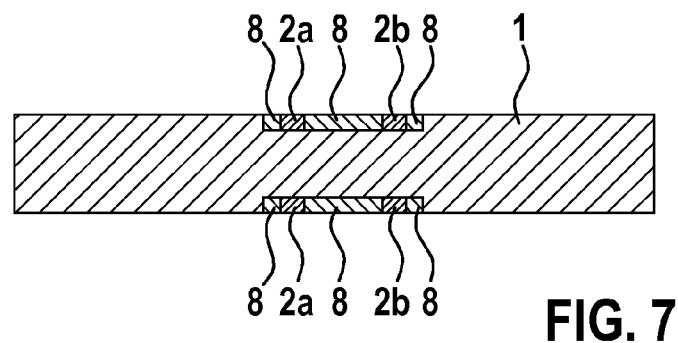

FIG. 7 shows a semi-finished product comprising a first layer element 1 and, in a recess, comprising two second layer elements 2a, 2b, which include high-temperature solders having different compositions. For example, the high-temperature solders can differ with regard to the compositions thereof, and optionally also with regard to the melting points thereof. The recess is filled by third layer elements 8 made of ductile material (such as, for example, aluminum), which ensures better formability during forming, such as circular embossing, of the pin. The ductile material moreover prevents the material of the respective second layer element 2a, 2b from flowing away laterally during circular embossing. It is thus ensured that the distribution of the respective second layer element 2a, 2b after forming is homogeneous and even around the pin.

Figure 8:
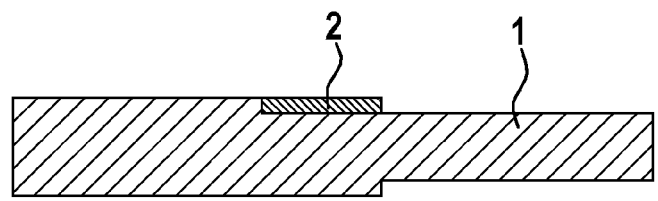

In the exemplary embodiment shown in FIG. 8, the second layer element 2 is disposed on an edge of the first layer element 1 so as to extend flush on one side with the surface of the first layer element 1. The first layer element 1 is thus profiled by the step in the region of the surface thereof.

Figure 9:
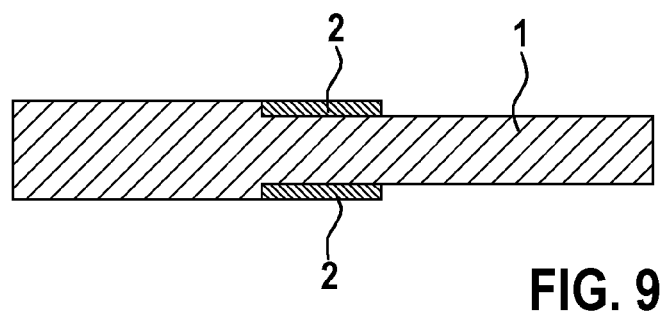

FIG. 9 shows a semi-finished product in which the second layer element 2 is integrally joined to an edge of the first layer element 1. This positioning can take place on maximally two sides of the semi-finished product, as shown. Due to the placement at the edge, the high-temperature solder of the second layer element 2 is given a preferred direction during melting. The solder will distribute predominantly in the plane of the respective second layer element 2.

Figure 10:
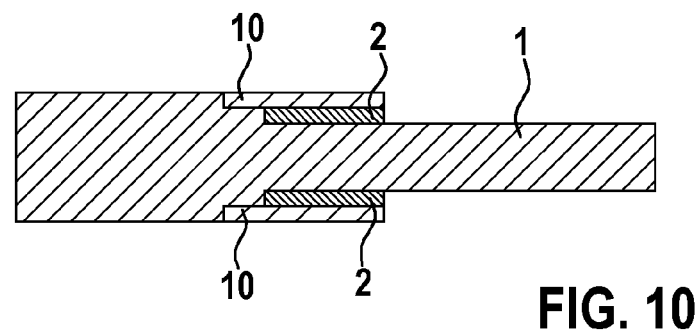

In the exemplary embodiment shown in FIG. 10, a top coat 10, which is applied to the first layer element 1 and to the second layer element 2 by way of joining, is provided in the region of the second layer element 2 and of the adjoining first layer element 1. By profiling of the first layer element 1, disposing the second layer element 2 directly at the edge of the first layer element 1 and providing the top coat 10, a preferred direction is defined for the melting or flowing out of the solder of the second layer element 2 (e.g., from left to right). Contraction due to surface tension of the solder is prevented by the top coat 10. The solder is protected from environmental influences (such as, for example, oxidation, damage, etc.) by the top coat 10 until melting.

Figure 11:
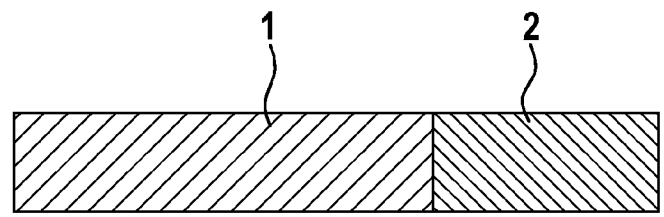

FIG. 11 shows an exemplary embodiment in which a first layer element 1 in the form of a biocompatible, electrically conducting layer 1 is connected and joined to a second layer element 2 disposed next to the same in the form of a nickel layer as a soft-solderable material. In this way, an end section of the pin according to this embodiment is designed as a nickel section and can thus be brazed well to a contact of a printed circuit board. As is apparent from FIG. 11, the cross-section of the second layer element is rectangular.

Figure 12:
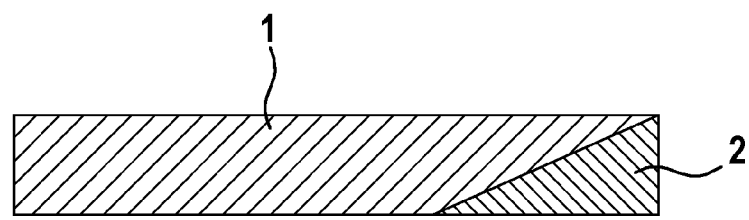
Figure 13:
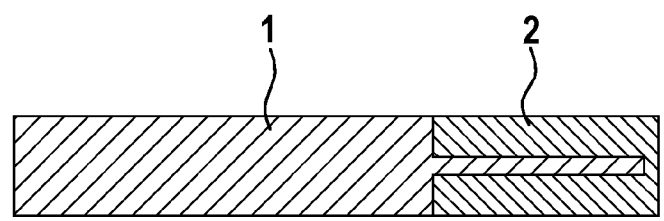

The exemplary embodiments shown in FIGS. 12-13 illustrate other shapes of the second layer element 2, the cross-section being triangular in FIG. 12 and U-shaped in FIG. 13. In particular in the case of the triangular cross-section, a transition in terms of the material from the electrically conducting material of the first layer element 1 to the soft-solderable material of the second layer element 2 is achieved.

Figure 14:
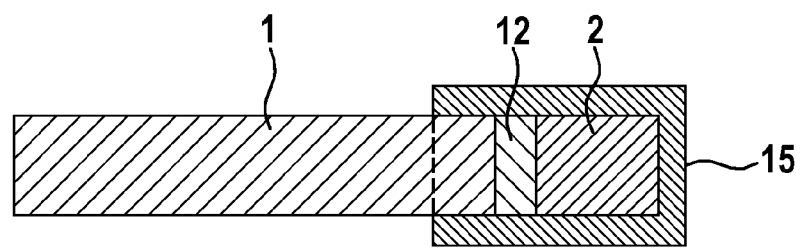
Figure 15:
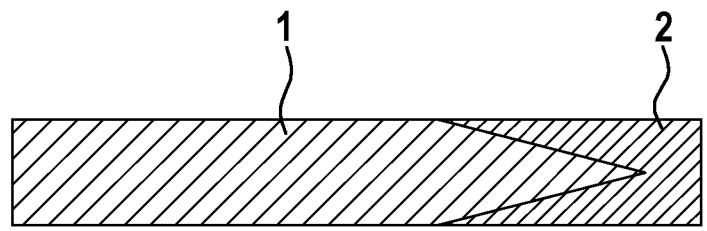

FIG. 14 shows that a diffusion zone 12, in which interdiffusion of the materials of the two layer elements 1, 2 takes place, can be formed between the first layer element 1 and the second layer element 2 by corresponding procedural steps, such as, for example, annealing.

Figure 16:
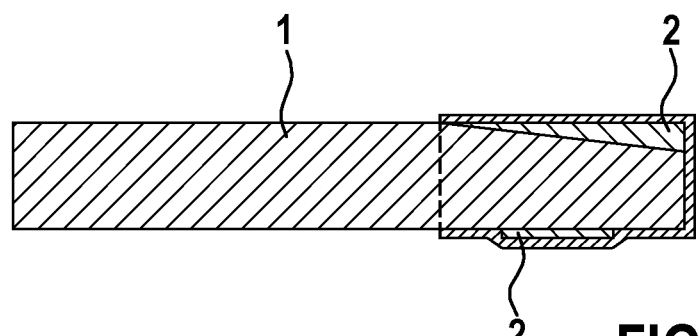
Figure 17:
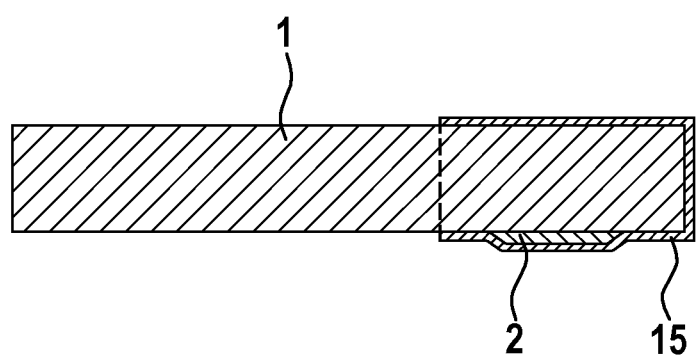

In the exemplary embodiments shown in FIGS. 14 and 16-17, a coating 15 is additionally provided, which represents corrosion protection for the second layer element 2, which frequently comprises Ni, for example, in the form of a Pd layer. Such a layer can be applied by way of CVD or PVD, for example.

Instead of the solder layer, the arrangement variants shown in FIGS. 1, 4-5, 8-9 and 10 are also conceivable for the arrangement of a second layer element 2 in the form of a soft-solderable layer.

Figure 18:
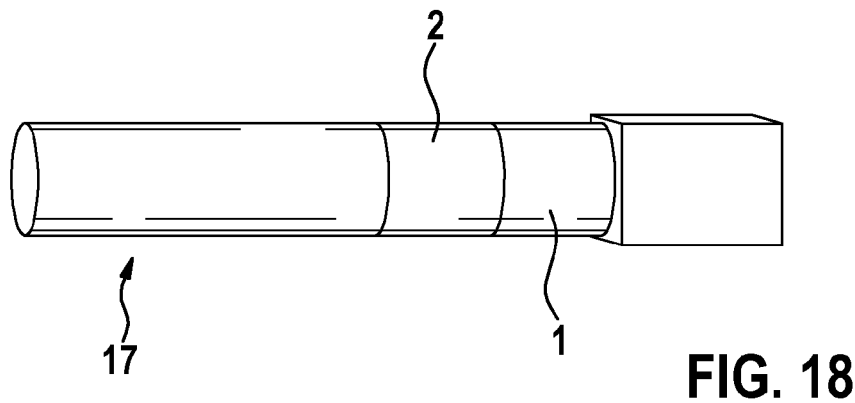
FIG. 18 shows a perspective side view of a further embodiment of a pin according to the present invention.

FIG. 18 shows an exemplary embodiment of a pin according to the present invention in which the end section 17, with which the pin can be placed through the insulator 20 of the feedthrough is circular-embossed after detachment from the semi-finished product. The second layer element 2 is located in a circular-embossed region, so that the solder is able to spread substantially evenly in the ceramic element. The region opposite the circular-embossed end section 17 still has the original contour of the starting material.

Figure 19:
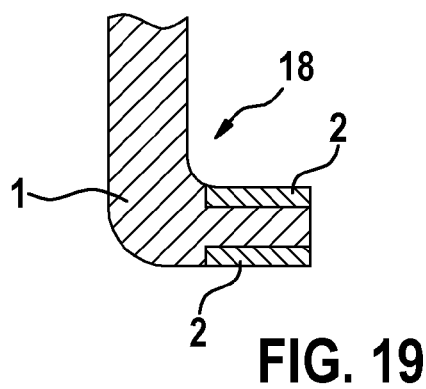
FIGS. 19-20 show a view from the side of an end section of a further exemplary embodiment of a pin according to the present invention prior to being brazed to the terminal of a printed circuit board (FIG. 19) and after brazing (FIG. 20)
Figure 20:
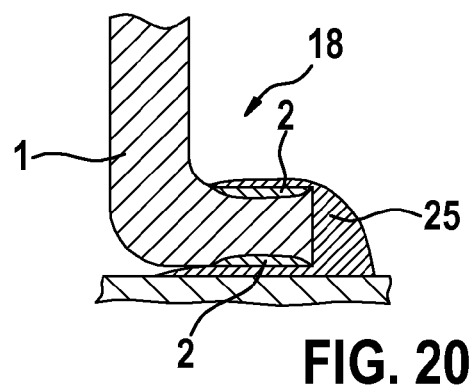
Figure 21:
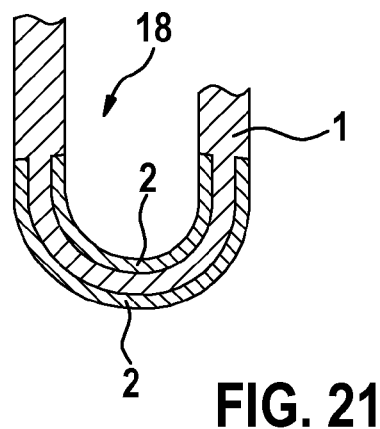
Figure 22:
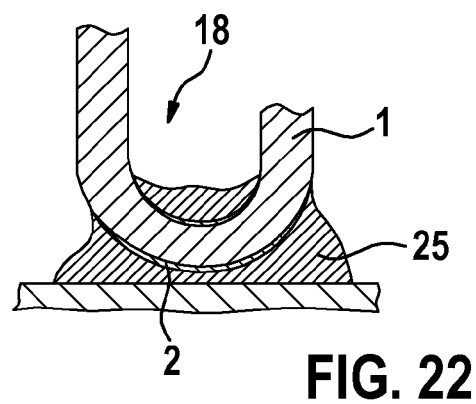
Figure 26:
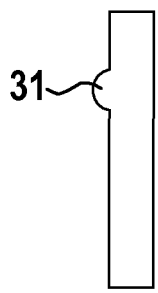
Figure 27:
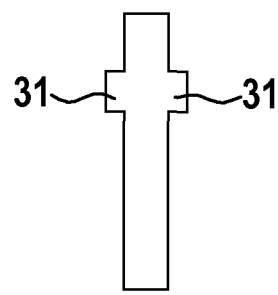
Figure 28:
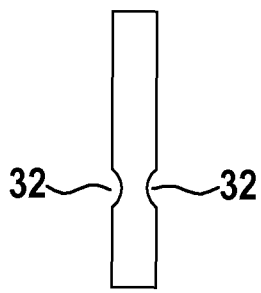
Figure 29:
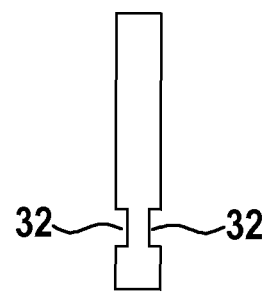
Figure 30:
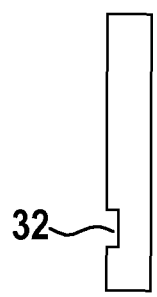
Figure 31:
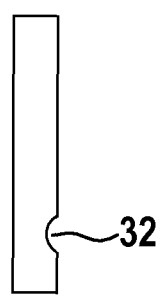

FIGS. 19, 21 and 23 show different exemplary embodiments of pins according to the present invention, the end section 18 of which, which is to be connected to a terminal of a printed circuit board, was formed into a predefined shape after detachment from the semi-finished product. The end section 18 shown in FIG. 19 has a rounded area in the shape of the segment of a quarter circle, similarly to what is known as the SOP shape. In FIG. 21, the end section 18 has what is known as a J-lead shape, and in FIG. 23, it has what is known as a gull wing shape. As described above, the arrangement of the soft-solderable material as the second layer element 2, as is apparent from the Figures, initially takes place by way of application to a semi-finished product and then detachment therefrom. The final pin geometry is established by forming (such as, for example, bending, upsetting, etc.). The position of the easily soft-solderable materials on the pin can be influenced by the joining of the materials and by the forming process. FIGS. 20, 22 and 24 in each case show the state after which the end section 18 of the respective pin was brazed to a terminal or pad of the printed circuit board. The printed circuit board is not shown separately. It is apparent that the easily soft-solderable material of the second layer element 2 causes good wetting and adhesion promotion between the pin and the printed circuit board. The solder cone 25 can thus develop beyond the second element 2.

Figure 34:
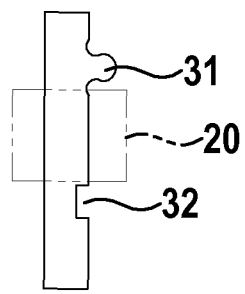
Figure 35:
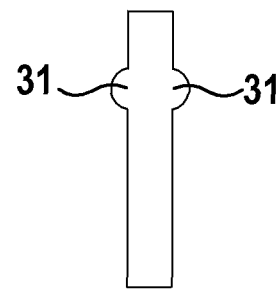
Figure 36:
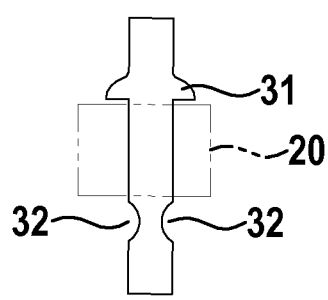
Figure 37:
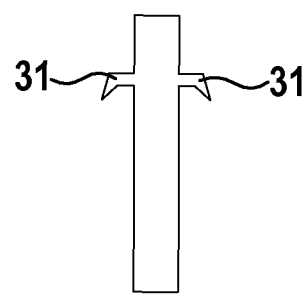
Figure 41:
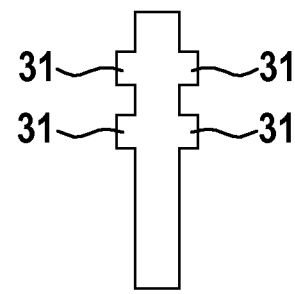
Figure 42:
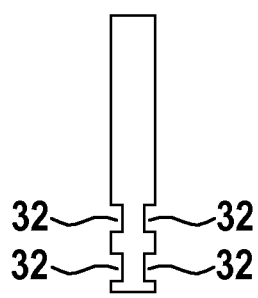
Figure 43:
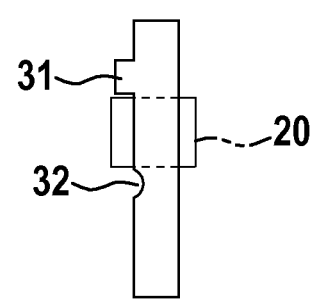
Figure 44:
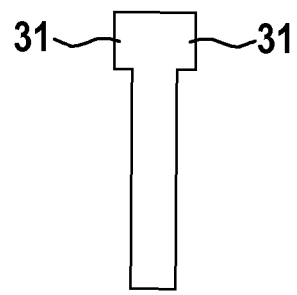

It is further advantageous if the semi-finished product is formed prior to detachment, or if the pin is formed after partial or complete detachment from the semi-finished product, so that a protrusion 31 and/or a recess 32 are created. FIGS. 25-31 and 34-46 show different variants of such protrusions 31 or recesses (cavities) 32. They can be provided at various locations on the outer side (lateral face) of the pin in the direction of the longitudinal axis. To this end, a protrusion 31 achieves that the pin acts as a stop during brazing into the feedthrough, as is shown in FIGS. 34 and 36, and that the pin holds itself in position during the brazing process. Moreover, as is shown in FIG. 44, a protrusion 31 in the end section of a pin can serve as a weld lip. Multiple protrusions 31 (see FIG. 41) at the end of the pin can assume the function of a crimp tab or a cooling fin for a downstream welding process.

A recess 32 can serve as a solder stop and inhibit spreading of the solder. The protrusion 31 and/or the recess 32 can be designed both individually, which is to say in the form of individual projections or troughs, or circumferentially in the form of a protruding web or notch or depression. A protrusion 31 or a recess 32 is preferably provided in the region of the first layer element 1; however, these can also extend into the region of the second layer element. The protrusion 31 or the notch 32 can have a round, an angular or any arbitrary (see FIG. 34) cross-section. FIGS. 34, 36 and 43 additionally indicate the position of the insulator 20 in the feedthrough after the pin has been inserted. It is apparent that the protrusion 31 holds the pin in position in the body 20 of the feedthrough. In the embodiment variants shown in FIGS. 36 and 43, the protrusion 31 was generated with a defined cross-section, so that the protrusion 31 is suitable for correctly positioning the body 20 of the feedthrough.

Figure 45:
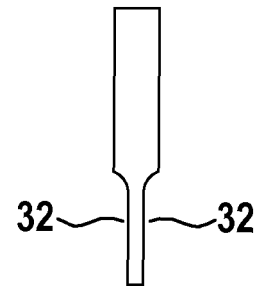
Figure 46:
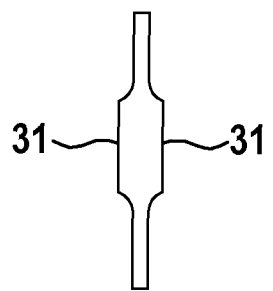

As is shown in FIGS. 44-46, the protrusion 31 and the recess 32 can also be implemented in the form of a widened area or narrowed area of the pin.

Figure 32:
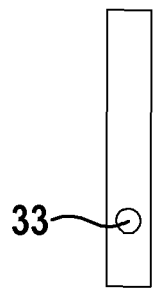
Figure 33:
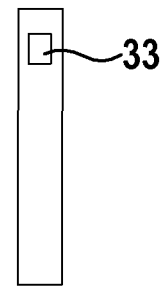
Figure 47:
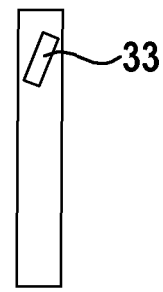

Moreover, predetermined breaking points can be provided in the form of continuous cut-outs 33, as is shown in FIGS. 32-33 and 47, which are intended to prevent the electromedical implant from leaking when the pin is torn off. The predetermined breaking points are provided in a section of the pin that is located so far on the outside, which is to say away from the housing interior, that hermetic sealing of the housing of the implant continues to be assured.

Figure 48:
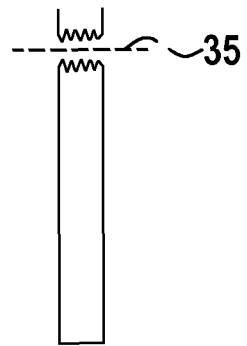
FIGS. 48-51 show views from the side of sections of further exemplary embodiments of pins according to the present invention.
Figure 49:
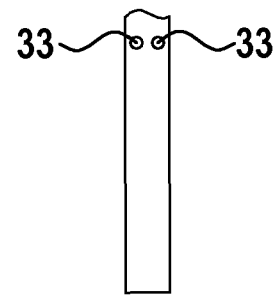
Figure 50:
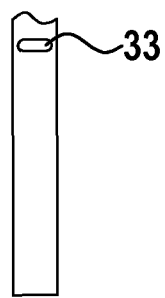
Figure 51:
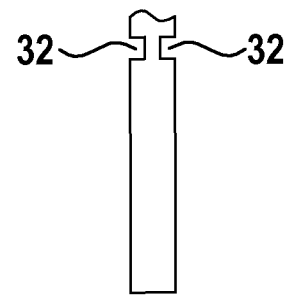

Further predetermined breaking points in the form of a continuous cut-out 33 or a recess 32 are shown in FIGS. 49-51. These are intended to detach the respective pin from the connecting web (indicated by the dotted line 35 in FIG. 48). The predetermined breaking points shown as continuous cut-outs 33 can alternatively also be implemented as notches.

Figure 38:
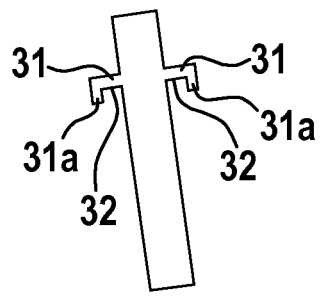
Figure 39:
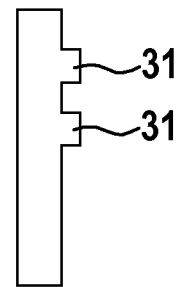
Figure 40:
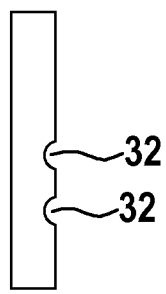

FIG. 38 shows a pin in the form of a sword having a "hilt" "crossguard" and "blade" (shaft). The "crossguard-like" recess 32 serves as a support and for alignment in the body 20 of the feedthrough. The downwardly directed extension 31a of the protrusion 31 is used for engagement or cradling in the body 20 of the feedthrough. The "blade region" of the pin is introduced into the body 20 of the ceramic and is therefore preferably designed to be round. The connection of the header takes place in the region of the "hilt", preferably by way of laser welding.

Figure 52:
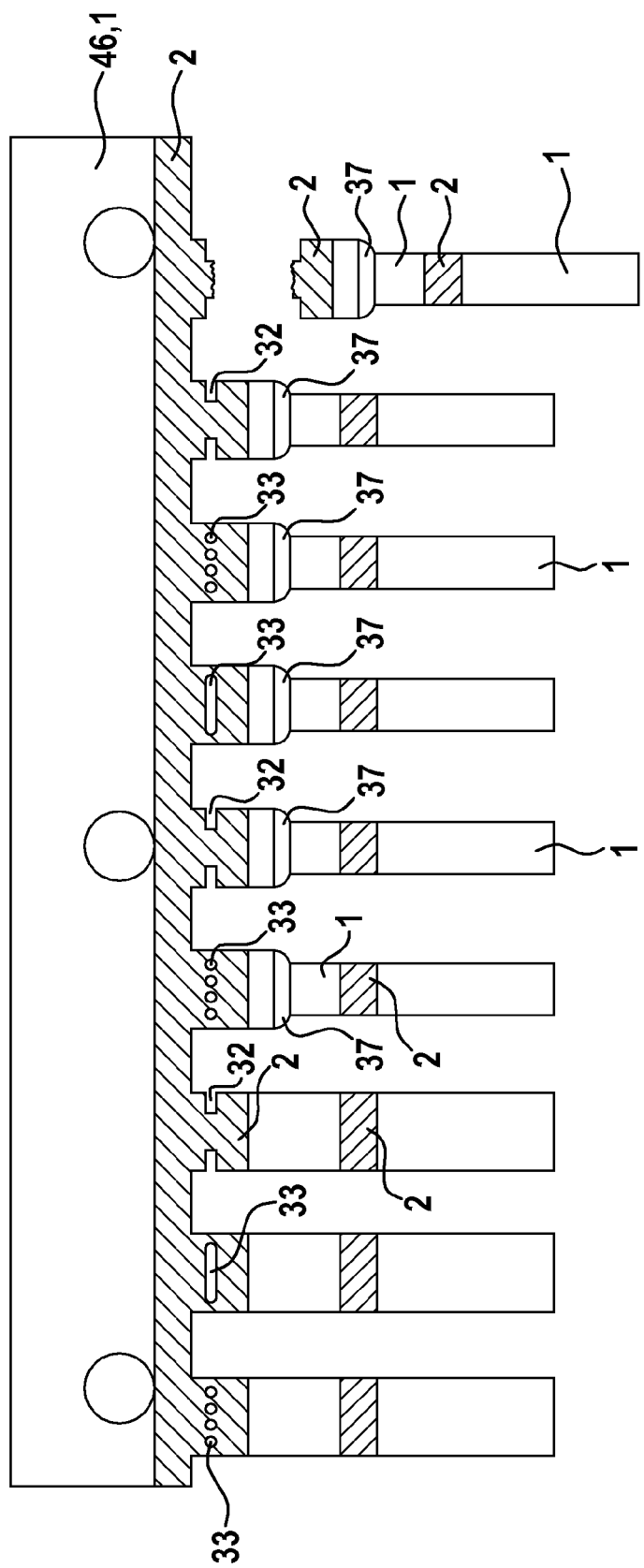
FIG. 52 shows a view from above of a section of a semi-finished product for producing pins according to the present invention, which illustrates different steps of the production of a pin.

FIG. 52 shows a perforation comb, which is comprised of the semi-finished product comprising partially detached pins (cut clear by way of punching, for example). The region of the semi-finished product located at the top in FIG. 52 forms a connecting web 46. The pins shown in FIG. 52 are shown by way of example in different stages of manufacture and with different design options of the predetermined breaking point, which is implemented by way of continuous cut-outs 33, for example. The three pins shown on the left side are shown after partial detachment (punching) from the semi-finished product. Pins four to eight (counting from the left) have a shaped area in the region 37 and are shortened after the forming process, by way of renewed punching, for example. The pin shown on the farthest right was broken out of the perforation comb along the predetermined breaking point and thereby completely detached from the semi-finished product.

Figure 53:
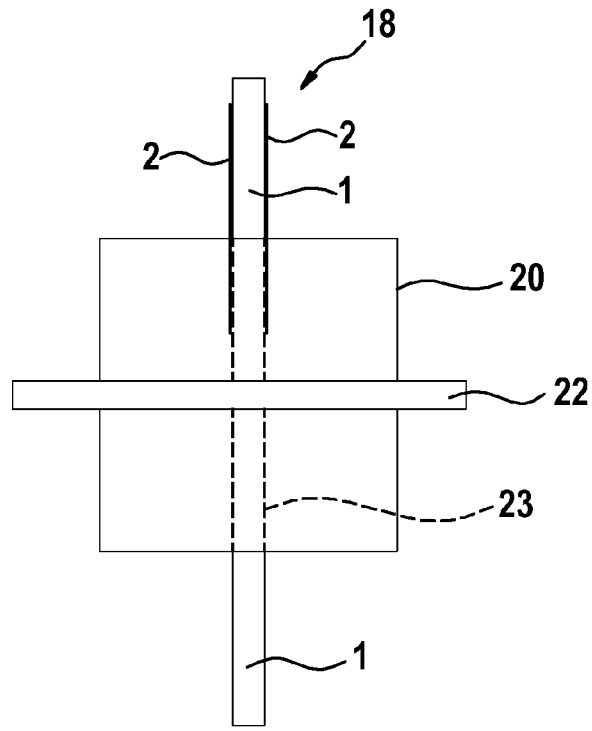
FIGS. 53-55 show views from the side of three exemplary embodiments of feedthroughs according to the present invention.
Figure 54:
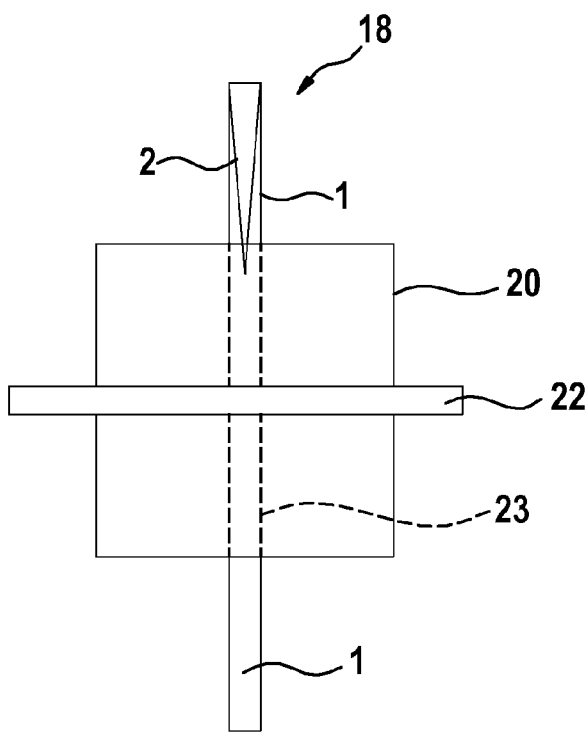

FIGS. 53-54 show a pin according to the present invention disposed in a feedthrough comprising a body 20 made of ceramic material. The body comprises a circumferential flange 22 for arrangement in the housing of an implant. The pin is seated in a continuous cut-out in the form of a borehole 23 in the body 20, wherein the two ends of the pin protrude from the body 20 in the longitudinal direction. At the end 18 facing the printed circuit board, the pin comprises a second layer element 2 in the form of a soft-solderable material, which facilitates brazing to a terminal of the printed circuit board.

Figure 55:
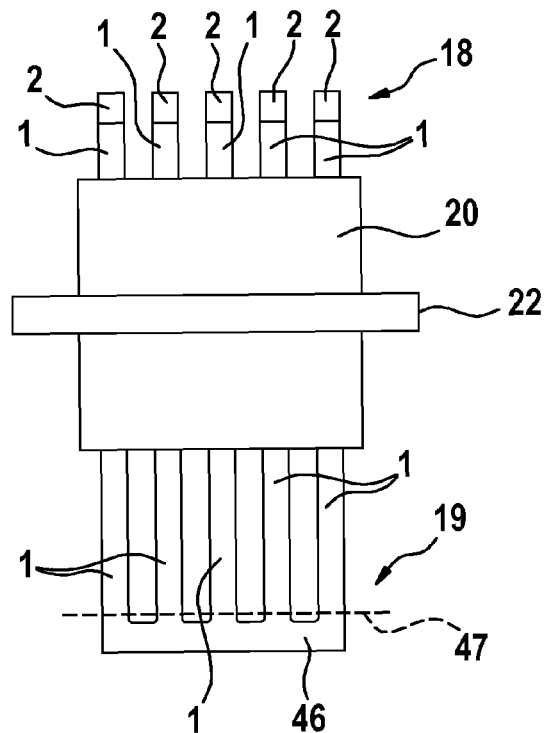
Figure 56:
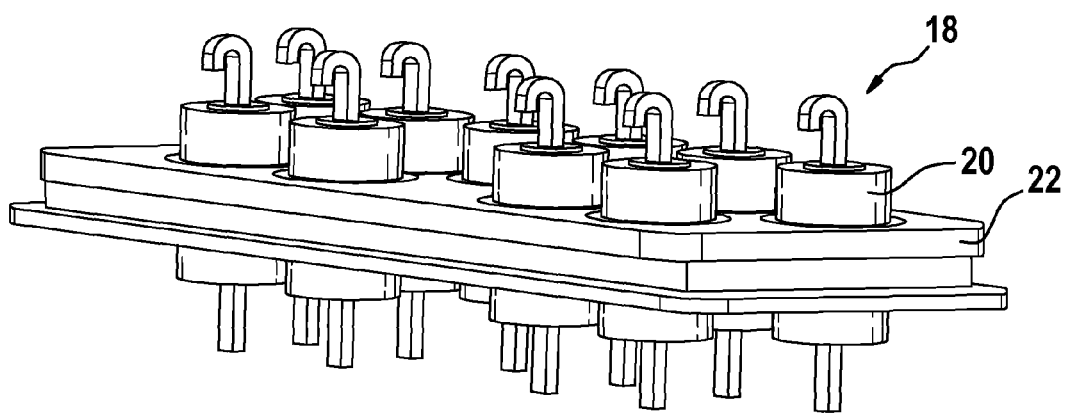
FIG. 56 shows a perspective side view of a further exemplary embodiment of a feedthrough according to the present invention.
Figure 57:
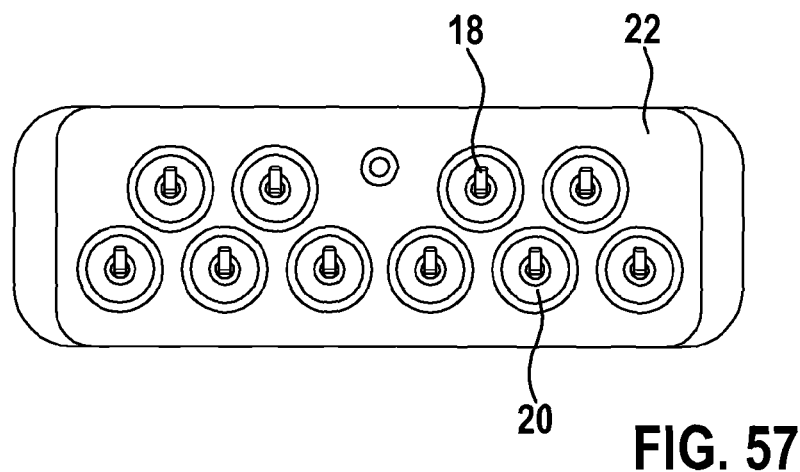
FIG. 57 shows a view from above of the exemplary embodiment of a feedthrough according to the present invention from FIG. 56.
Figure 58:
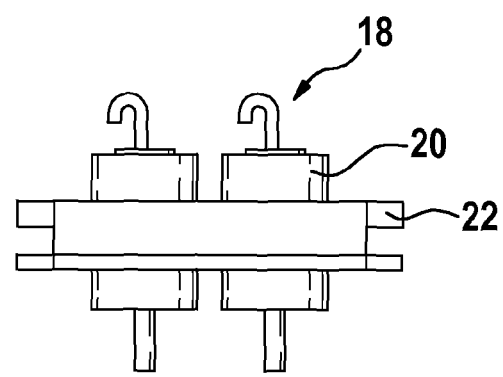
FIG. 58 shows a view from the side onto the exemplary embodiment of a feedthrough according to the present invention from FIG. 56.
Figure 59:
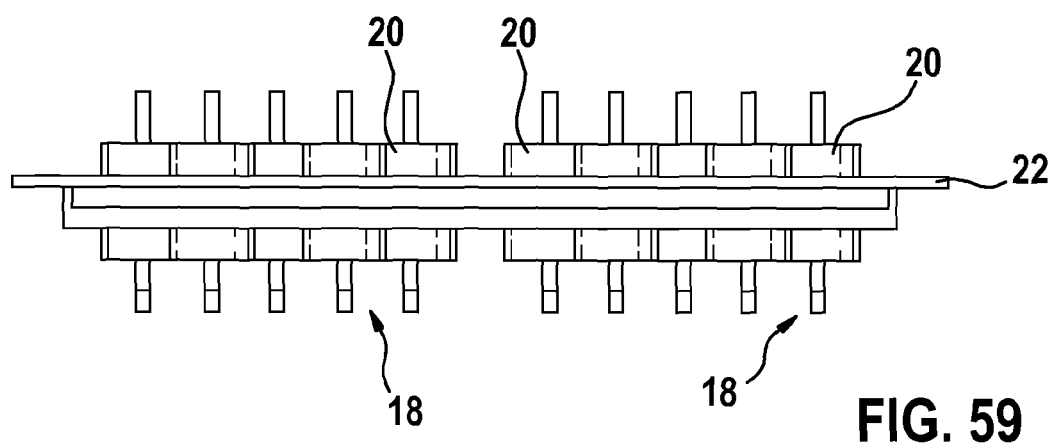
FIG. 59 shows a further view from the side of the exemplary embodiment of a feedthrough according to the present invention from FIG. 56.

FIG. 55 shows a feedthrough comprising a set of pins, which are connected in the end section 19 at the end facing away from the printed circuit board by way of a connecting web 46. After brazing the pins in the body 20 of the feedthrough, these are detached from each other along the separating line 47 (dotted). So as to implement the connecting web 46, the pins are detached only partially from the semi-finished product, as is shown in FIG. 52, so that a region of the semi-finished product remains as the connecting web 46.

The further exemplary embodiment of a feedthrough according to the present invention shown in FIGS. 56-59 comprises a flange 22, which is used to dispose the feedthrough in the electromedical implant, and cylindrical ceramic bodies 20, into each of which a pin is brazed. Each pin has a hook-shaped end section 18 at the end facing the printed circuit board, the end section being designed as a J-lead. The end section can also be used to orient the pin with respect to the feedthrough and align it. The pin is later joined with the printed circuit board at the end section 18. In this region, as is shown in FIG. 21, the pin comprises a second layer element, which can be easily wetted with soft solder.

Figure 60:
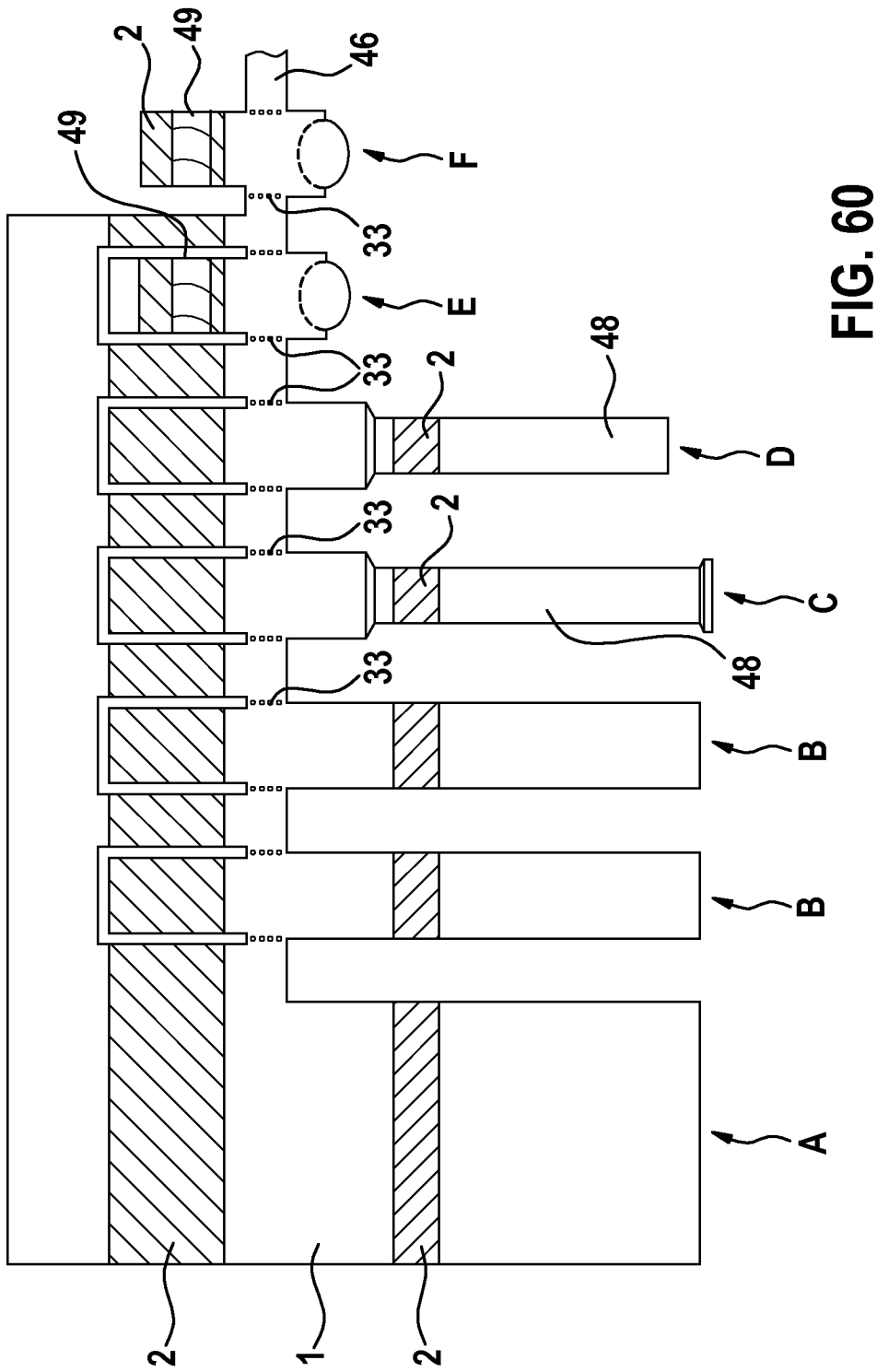
FIG. 60 shows a view from above of a section of a semi-finished product for producing pins according to the present invention, which illustrates different steps (A to F) of the production of a pin.

FIG. 60 illustrates the steps of producing a pin according to the present invention by way of an integrated punching-and-bending process. Proceeding from the sheet-shaped semi-finished product (see step A) comprising the sheet-shaped first layer element 1 made of an electrically conducting material and two second layer elements 2, which are joined thereto and made of two strips and which are disposed on the first layer element 1 and include a solder or a soft-solderable material, the pin is produced in steps by way of punching or forming. For this purpose, first the contour of the respective pin is partially detached from the semi-finished product (for example, cut out by way of punching, see step B), and thereafter the shaft 48 of the pin is turned into a round shape by way of forming (see step C). This region is used for insertion into the insulator of the ceramic and will thus be smaller by approximately 0.05 to 0.4 mm in terms of the diameter than the borehole in the insulator so as to achieve a solder gap appropriate for joining. After circular embossing, the length of the pin must be readjusted by way of severing (cutting to length, such as, for example, by way of punching, see step D), since the forming process results in a change of length in the direction of the pin axis. By way of bending, the shaft 48 of the pin (downward in FIG. 60) and the upper end section 49 of the pin comprising the soft-solderable second layer element 2 are formed to obtain a J-lead (step E). Finally, the superfluous material of the semi-finished product can be removed (step F). A connecting web 46 in the form of a belt connects the finished pins and serves as an assembly aid for simultaneously positioning multiple components. The belt can be removed at the predetermined breaking points, which are formed by way of continuous cut-outs 33 or material tapers.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS AND SYMBOLS 1 first layer element
2 second layer element
2a, 2b second layer element
3 adhesion layer element
4 anti-wetting layer element
5 separating edge
6 top coat
8 third layer element made of ductile metal
10 coating
12 diffusion zone
15 coating
17 end section of the pin
18 end section of the pin
19 perforation comb
20 body of the feedthrough
22 flange
23 borehole
25 solder cone
31 protrusion
31a extension
32 recess
33 continuous cut-out
35 dotted line (shear edge)
37 region comprising formed area
46 connecting web
47 separating line
48 shaft of the pin
49 end section of the pin
A, B step in the production of a pin according to the invention
C, D step in the production of a pin according to the invention
E, F step in the production of a pin according to the invention

We claim:
1. A method for producing a pin, or a set of multiple pins for a feedthrough for an electromedical implant, the method comprising the following steps:
    creating a sheet- or strip-shaped semi-finished product by joining at least one first layer element comprising an electrically conducting and biocompatible material in sheet or strip form and at least one second layer element comprising an easily soft-solderable material in sheet or strip form;

applying at least one solder inhibitor layer element in sheet or strip form to the semi-finished product and optionally joining the at least one solder inhibitor layer element thereto; and at least partially detaching a pin, or a set of multiple pins connected to a connecting web, from the semi-finished product.

2. The method according to claim 1, wherein the at least one solder inhibitor layer element in sheet or strip form is joined to the semi-finished product.

3. The method according to claim 1, wherein the semi-finished product additionally comprises at least one third layer element including an insulator or a ductile metal, which is joined with the at least one first layer element.

4. The method according to claim 1, wherein a top coat is applied to the semi-finished product by way of an electroplating bath, prior to the at least partial detachment of the pin, or of the set of multiple pins, from the semi-finished product.

5. The method according to claim 4, wherein the top coat is applied to at least a portion of the at least one second layer element.

6. The method according to claim 1, wherein the pin, or at least one pin of the set of multiple pins, is formed prior to or after being at least partially detached from the semi-finished product in such a way that the at least one second layer at least partially surrounds the pin.

7. The method according to claim 6, wherein the pin, or each pin of the set of multiple pins, is formed after the at least partial detachment in such a way that at least one circumferential protrusion is created, the protrusion being located in each case on the side surface of the particular pin.

8. The method according to claim 3, wherein the at least partial detachment takes place in a direction that is substantially perpendicular to the direction of joining of the at least one first layer element with the at least one second element.

9. The method according to claim 1, wherein a section of the pin is turned into a round shape by way of forming after the at least partial detachment.

10. The method according to claim 1, wherein the pin is formed on at least one end section into a gull wing, J-lead or SOP-like shape after the at least partial detachment.

11. The method according to claim 1, wherein a predetermined breaking point is introduced into an end section of a pin of the set of multiple pins connected to a connecting web.

12. A method for producing a feedthrough for an electromedical implant, wherein a body of a feedthrough having at least one continuous cut-out is provided, comprising producing a pin in according to claim 1, and carrying out an additional step, according to which the pin, or each pin of the set of multiple pins, is subsequently connected to the inner surface of a continuous cut-out of the insulator by way of brazing.

13. The method according to claim 12, wherein the multiple pins are subsequently detached from each other.

14. A method for producing an electromedical implant comprising a printed circuit board, comprising producing a feedthrough according to claim 12, and wherein subsequently each pin of the feedthrough is connected to a terminal of the printed circuit board by way of brazing or welding.

15. A pin for an electromedical implant, produced using the method according to claim 1.

16. A feedthrough for an electromedical implant, produced using the method according to claim 12.

17. An electromedical implant, produced using the method according to claim 14.

18. The method according to claim 1, wherein the semi-finished product additionally comprises at least one third layer element including an insulator or a ductile metal, which is joined with the at least one second layer element.

19. The method according to claim 1, wherein a top coat is applied to the semi-finished product by way of an electroplating bath, after the at least partial detachment of the pin, or of the set of multiple pins, from the semi-finished product.

20. The method according to claim 6, wherein the pin, or each pin of the set of multiple pins, is formed after the at least partial detachment in such a way that at least one circumferential recess is created, the recess being located in each case on the side surface of the particular pin.

21. The method according to claim 3, wherein the at least partial detachment takes place in a direction that is substantially perpendicular to the direction of joining of the at least one third layer element.

22. A method for producing a pin, or a set of multiple pins for a feedthrough for an electromedical implant, the method comprising the following steps:

creating a sheet or strip shaped semi-finished product by applying at least one second layer element comprising an easily soft solderable material in sheet or strip form, onto at least one first layer element comprising an electrically conducting and biocompatible material in sheet or strip form;

applying at least one solder inhibitor layer element in sheet or strip form to the semi-finished product and optionally joining the at least one solder inhibitor layer element thereto; and at least partially detaching a pin, or a set of multiple pins connected to a connecting web, from the semi-finished product.

23. A method for producing a pin, or a set of multiple pins for a feedthrough for an electromedical implant, the method comprising the following steps:

creating a sheet or strip shaped semi-finished product by joining at least one first layer element comprising an electrically conducting and biocompatible material in sheet or strip form and at least one second layer element comprising a solder material in sheet or strip form;

applying at least one solder inhibitor layer element in sheet or strip form to the semi-finished product and optionally joining the at least one solder inhibitor layer element thereto; and at least partially detaching a pin, or a set of multiple pins connected to a connecting web, from the semi-finished product.

24. A method for producing a pin, or a set of multiple pins for a feedthrough for an electromedical implant, the method comprising the following steps:

creating a sheet or strip shaped semi-finished product by applying at least one second layer element comprising a solder material in sheet or strip form, onto at least one first layer element comprising an electrically conducting and biocompatible material in sheet or strip form;

at least one solder inhibitor layer element in sheet or strip form is applied to the semi-finished product and optionally joined thereto; and at least partially detaching a pin, or a set of multiple pins connected to a connecting web, from the semi-finished product.

* * * * *